(12) United States Patent
Puppini et al.

(10) Patent No.: US 8,881,600 B2
(45) Date of Patent: Nov. 11, 2014

(54) APPARATUS AND PROCESS FOR TESTING FILTERS

(75) Inventors: Anna Puppini, Mirandola (IT); Renato Pedrazzi, Mirandola (IT); Mauro Suffritti, Medolla (IT)

(73) Assignee: Gambro Lundia AB, Lund (SE)

( * ) Notice: Subject to any disclaimer, the term of this patent is extended or adjusted under 35 U.S.C. 154(b) by 901 days.

(21) Appl. No.: 11/993,204

(22) PCT Filed: Jul. 1, 2005

(86) PCT No.: PCT/IB2005/001887
§ 371 (c)(1),
(2), (4) Date: Dec. 19, 2007

(87) PCT Pub. No.: WO2007/003980
PCT Pub. Date: Jan. 11, 2007

(65) Prior Publication Data
US 2009/0151470 A1      Jun. 18, 2009

(51) Int. Cl.
*G01F 1/00* (2006.01)
*A61M 1/34* (2006.01)

(52) U.S. Cl.
CPC ........... *A61M 1/34* (2013.01); *A61M 2205/705* (2013.01)
USPC .... 73/861; 73/863.23; 73/864.34; 210/321.6; 210/637; 210/645; 210/646; 604/4.01; 604/5.01; 604/6.01

(58) Field of Classification Search
CPC .......................... A61M 1/34; A61M 2205/705
USPC .............. 210/321, 637, 645, 646; 604/4, 5, 6; 73/861, 863.23, 864.34
See application file for complete search history.

(56) References Cited

U.S. PATENT DOCUMENTS

| | | | |
|---|---|---|---|
| 4,614,109 A | 9/1986 | Hofmann | |
| 4,702,829 A | 10/1987 | Polaschegg et al. | |
| 4,834,888 A | 5/1989 | Polaschegg | |
| 5,064,529 A | 11/1991 | Hirayama et al. | |
| 5,580,460 A * | 12/1996 | Polaschegg | 210/646 |
| 5,594,161 A | 1/1997 | Randhahn et al. | |
| 5,702,597 A | 12/1997 | Chevallet et al. | |
| 5,808,181 A | 9/1998 | Wamsiedler et al. | |
| 6,228,271 B1 | 5/2001 | Cote | |

FOREIGN PATENT DOCUMENTS

| | | |
|---|---|---|
| DE | 34 42 744 A1 | 6/1986 |
| DE | 695 34 830 T2 | 10/2006 |
| EP | 0 189 561 A1 | 8/1986 |
| EP | 0 270 794 A2 | 6/1988 |
| EP | 0 407 737 B1 | 1/1991 |
| EP | 0 491 981 B1 | 7/1992 |

(Continued)

*Primary Examiner* — Dirk Bass
(74) *Attorney, Agent, or Firm* — Pearne & Gordon LLP (57) ABSTRACT

In a process for testing filters (4) and (13) of treatment fluid of a hemodiafiltration apparatus (1), each filter has a wet semi-permeable membrane (5, 14) which separates a gas-filled first chamber (6 and 15) from a liquid-filled second chamber (7 and 16). The first chambers are pressurised by a pump (19) supplying air, while the second chambers are placed in depression by a drainage pump (17) of used dialysis fluid. A first closed system is formed which includes the first chambers and a second closed system is formed which includes the second chambers. Two pressure gauges (P1 and P2) monitor the pressure in the two closed systems for a predetermined time. The monitoring provides indications relating to the filter integrity.

16 Claims, 8 Drawing Sheets

(56) References Cited

FOREIGN PATENT DOCUMENTS

| | | | |
|---|---|---|---|
| EP | 0 763 367 | A1 | 3/1997 |
| EP | 1 300 167 | A2 | 4/2003 |
| JP | 61-203973 | A | 9/1986 |
| JP | 7-79835 | B2 | 8/1995 |
| JP | 8-52207 | A | 2/1996 |
| JP | 8-187284 | A | 7/1996 |
| JP | 9-164198 | A | 6/1997 |
| JP | 2002-126076 | A | 5/2002 |

\* cited by examiner

APPARATUS AND PROCESS FOR TESTING FILTERS

BACKGROUND OF THE INVENTION

The invention relates to an apparatus and a process for testing filters.

Specifically, though not exclusively, the invention can be usefully applied for filters of an apparatus for extracorporeal blood treatment, in particular for membrane filters normally used in a device for on-line preparation of a dialysis liquid and/or a replacement liquid, in the ambit of an apparatus for hemodialysis and/or hemo(dia)filtration, with the aim of removing germs contained in the liquid.

Membrane filters are used in the production of sterile liquids, by causing the liquid to pass through a semi-permeable membrane able to filter the germs. Also known are various processes for checking the characteristics of the membrane of a filter in order to guarantee its efficiency in treating the germs.

One of the known processes is the bubble point test (BPT), which can check on the absence of membrane pores having pores which have a greater size than a predetermined limit. The BPT considers the membrane pores as capillary tubes, and the maximum radius of the pores is determined by pressure measurements. The test briefly comprises the following stages: the membrane is wetted so that the pores are full of liquid; a first side of the membrane is connected to a gas source, while the opposite side is connected to a liquid for easy detection of gas bubbles; the first side of the membrane is gradually pressurised with the gas; while the gas pressure on the first side remains relatively low, a modest amount of gas will displace, by diffusion, through the liquid contained in the membrane pores towards the second side of the membrane; this amount of gas flow is proportional to the speed of increase of gas pressure on the first side; when the gas pressure reaches a certain level, the liquid contained in the largest pores is forced to exit from the pores themselves, and a considerable amount of gas crosses the largest pores, reaching the liquid connected to the second side of the membrane, forming gas bubbles within the liquid; in this situation a further pressuring action leads to a further displacement of gas towards the second side of the membrane, with no discernible increase in pressure; the substantially stable pressure reached in this situation (bubble point pressure, or BP pressure) is a known function of the maximum radius of the membrane pores and thus enables determination thereof; stopping the pressurisation action leads to a situation of substantial equilibrium in the BP pressure.

Prior-art document U.S. Pat. No. 4,614,109 describes a process for checking the permeability of a wet membrane of a filter, based both on a search for the BP pressure and on the determination of the gas diffusion before reaching BP pressure. In this process, the filter membrane is first impregnated with liquid; thereafter, the inlet side of the membrane is gradually pressurised by introduction of a gas; the gas that passes by diffusion through the membrane is collected in a graduated container; the permeability of the membrane is calculated on the basis of the transmembrane pressure measured on the two sides o the membrane, and of the quantity of gas diffused through the membrane per unit of time using the graduated container. By continuing with the pressurisation, at a certain point (called the visual bubble point because it can be visually detected) the production of gas bubbles on the exit side of the membrane sharply increases: this, as mentioned above, is due to the fact that, on reaching the bubble point pressure, the passage of gas through the membrane occurs both by diffusion (in a small part) and (prevalently) by effect of the formation of gas conduits through the pores of the membrane.

U.S. Pat. No. 4,614,109 further describes a process by which the transmembrane pressure can be determined by pressure measurements performed only on the inlet side of the membrane, i.e. on the side which, in the case of a sterile filter, is considered non-sterile, with the aim of not contaminating the sterile side of the membrane by performing these measurements. This is done by measuring a pressure gradient between the inlet side of the membrane and a specific reference pressure system which at the outset of each test is connected to the gas source generating the test pressure.

U.S. Pat. No. 5,064,529 describes an automatic BPT (without the need to observe the moment of gas bubble formation) to check whether the effective BP pressure of the membrane corresponds to the desired BP pressure corresponding to the maximum diameter of the pores indicated by the membrane manufacturer; in a first stage the first side of the membrane is pressurised with the gas at a predetermined constant pressurisation speed, at the end of which first stage the pressure measured on the first side of the membrane should correspond to a predetermined theoretical pressure; the pressurisation speed and the pressurisation time are chosen so that the above-mentioned theoretical pressure is lower than the desired BP pressure; if the pressure measured after the predetermined time does not correspond to the theoretical pressure, a fault is signalled due, probably, to the breakage of the membrane or a faulty installation of the filter; in a second stage, the pressurisation is halted for a certain time period in which the pressure should remain substantially constant; if, on the contrary, there is a significant drop in pressure, a fault is signalled due, probably, to the faulty filling-up of the pores with the liquid; in a third stage, the pressurisation of the first side of the membrane is re-established at a predetermined speed for a predetermined time, during which theoretically the desired BP pressure is reached; if, at the end of the third stage, the desired BP pressure is measured, within a predetermined range of acceptability, it is considered that the maximum diameter of the pores is the desired one.

U.S. Pat. No. 5,594,161 describes a process for testing the integrity of one or more filtering elements in which the inlet side of the filter element is wetted and subjected to a gas pressure which is kept constant, while the pressure is measured on the outlet side which, previously, has been made part of a closed system. If, after a predetermined time, the outlet pressure does not exceed a predetermined threshold value, the filter element is considered intact.

U.S. Pat. No. 6,228,271 describes a process for testing the integrity of filter membranes in which the filter inlet chamber is emptied of liquid and filled with air at atmospheric pressure, while the outlet chamber remains full of liquid. A depression is then created in the outlet chamber in order to create a transmembrane pressure; after the depression has been stabilised, for example at a value comprised between 0.2 and 0.9 bar (absolute pressure), and before completely evacuating the liquid from the outlet chamber, the constant flow of liquid is measured as it exits the outlet chamber, which corresponds to the air flow passing through the perforations of the membrane; the integrity of the membrane is thus measured on the basis of the value measured for the liquid flow.

Another known process for measuring the integrity of a filter membrane is on the basis of a verification modality under sealed pressure, according to which a transmembrane pressure gradient is created and monitored over time in at least one chamber of the filter. A typical sealed pressure test involves, for example, a side of the membrane being brought up to a predetermined gas pressure, below BP pressure, comprised in the diffusion range, i.e. a range in which the pressure in the second membrane chamber increases proportionally to the pressure in the first side; when the pressure has been reached, the gas supply is interrupted and the pressure on the first side monitored; if the drop in pressure per time unit exceeds a predetermined threshold value, the membrane is understood to exhibit some defects.

U.S. Pat. No. 4,702,829 describes a process, of the pressurised sealed type, for verifying the integrity of the filters of a hemodiafiltration apparatus, in which the substitution liquid is realised on-line by passing the dialyser liquid through two sterile filters arranged one after another, each of which exhibits two chambers separated by a water-wettable and semipermeable membrane, which can hold the germs. The verification process of the filter seal begins after the dialysis circuit washing stage, with the circuit full of the detergent liquid and the water-wettable filter membranes wet. The filter seal verification process uses an ultrafiltration pump, predisposed in the dialysis circuit downstream of the blood treatment device and used in the dialysis treatment for obtaining a patient weight drop measurement. During the filter test, the ultrafiltration pump is used to aspirate air internally of the first chamber of the second filter, through a microporous water-repelling filter arranged in a breather of the first chamber. The aspirated air can also enter the second chamber of the first filter in the absence of occlusions in the circuit branch comprised between the two filters. The liquid that leaves space for the aspirated air is removed by the ultrafiltration pump through the membranes of the two filters. Given that the water-wettable membranes of the filters are wet; the membranes themselves are substantially impermeable to air. Therefore, once the second chamber of the first filter and the first chamber of the second filter are entirely occupied by air at atmospheric pressure, and since the air that has entered the chambers cannot escape through the membrane, the ultrafiltration pump can generate a depression in chambers occupied by the liquid, i.e. the first chamber of the first filter and the second chamber of the second filter. The ultrafiltration pump is then activated until a determined depression has been reached in a part of the dialysis circuit filled with liquid. Thereafter, the depression is monitored using a pressure gauge, for example by measuring the time necessary for the pressure to rise by a predetermined quantity, or by measuring the depression after a determined period of time. The monitoring of the depression enables an evaluation of the fluid seal of the system constituted by the membranes and the part of the circuit under depression.

U.S. Pat. No. 4,834,888 describes a control process of the integrity of a sterile filter arranged in the supply system of a dialyser liquid to a dialyser, according to which the dialyser is removed and the flow in the dialyser liquid circuit interrupted, by stopping the circulation pump or alternatively closing two intercept valves, one arranged on the fresh dialyser liquid supply line and the other on the used dialyser liquid drainage line, closing an intercept valve arranged on a rinse line which unites an exit of the first chamber of the sterile filter to the drainage line, opening a ventilation valve arranged in the rinse line between the outlet of the first chamber and the intercept valve, start up the ultrafiltration pump which during the dialysis treatment is used for calculating a patient's weight loss, and finally monitoring the pressure using a pressure gauge arranged on the drainage line. The ultrafiltration pump causes the inlet of air through the ventilation valve and thus inside the first chamber of the sterile filter, while the liquid contained in the first chamber is forced to pass through the membrane and thus internally of the second chamber. When the liquid has been expelled from the first chamber, the wet membrane, if intact, represents an air-impermeable barrier, so that the last action of the ultrafiltration pump causes a depression in the part of the circuit which is connected to the second chamber of the sterile filter; when the pressure gauge signals that a predetermined degree of depression has been reached, the ultrafiltration pump is stopped; if, after a predetermined period of time, the depression has not substantially change, the filter membrane is considered to be intact.

In EP 491981, which concerns a plant for the production of a concentrate for hemodialysis by mixing water with a soluble powder, a test is used for verifying the integrity of a filter which is part of the plant. The plant comprises a gas pump which can be used both for eliminating the gas which is freed during the production of the hemodialysis concentrate in a mixing tank, or for generating, in one of the two chambers of the filter, an overpressure which is monitored to evaluate the integrity of the filter membrane.

U.S. Pat. No. 5,808,181 describes a process for verifying membrane filters arranged in the dialysis circuit of a device for extracorporeal blood treatment, in which the membrane of a filter to be checked is completely wetted with a liquid, a branch of the dialysis circuit containing one of the two filter chambers to be verified is separated from the rest of the circuit, a gas is injected into the separated branch to cause an overpressure, while the liquid contained in the chamber is removed by passing through the membrane; the gas supply is interrupted after a predetermined overpressure level has been reached in chamber; thereafter, the overpressure is controlled, for example by comparing the pressure drop per time unit with a limit value which is characteristic of an intact filter membrane.

EP 407737 describes a process for testing the membrane of a dialyser filter in two stages: in a first stage the blood chamber of the dialyser is subjected to a pressure gradient from the blood chamber to the dialyser fluid chamber; in a second stage the membrane is subjected to an opposite gradient. The test enables a determination of the presence of leaks which might appear or be noted only by effect of one or other of the two pressure gradients.

SUMMARY OF THE INVENTION

A principal aim of the present invention is to provide a process for the testing of filters which is reliable and precise without the use of high pressures in the hydraulic circuit connected to the filter or filters. The aim is achieved by generating a transmembrane pressure of the filter to be tested by creating an overpressure on one side of the membrane and a depression on the opposite side thereof.

A further aim of the invention is to provide an apparatus which is simple and economical for actuating the above-described process.

An advantage of the invention is that it is applicable simply and economically for testing filters of apparatus for extracorporeal blood treatment, such as hemodialysis and hemo(dia) filtration apparatus.

A further advantage is that it also makes available a very precise and sensitive verification process for filters which are not suitable (because of breakages, leaks, excessive permeability or pore size, etc.) for relatively minor reasons. This advantage is attained by virtue of a test based on the reading of gas quantities and/or liquid in inlet and/or in outlet to or from the filter chambers.

A still further advantage is that the invention provides a process for checking which can be effected relatively rapidly. This is made possible firstly by the fact that the transmembrane pressure is generated using two actuators operating on the two opposite sides of the membrane, and secondly because the evacuation of the liquid from a filter chamber, which is necessary to cause the test gas to enter, is done by a tangential liquid flow which does not cross the membrane.

A further advantage is that the invention recognises whether the detection of a faulty situation is due to the unsuitablility of the membrane or whether it is due instead to leakages in other parts of the hydraulic circuit connected to the filter. This advantage is obtained by means of the independent monitoring of both sides of the membrane.

Furthermore, in the case of two consecutive filters (for example a first filter for the dialyser liquid and a second filter for the replacement liquid in a hemo(dia)filtration apparatus), the invention advantageously enables detection of which, if one only, of the two filters is at fault, and indeed if only one of them is faulty.

Further characteristics and advantages of the present invention will better emerge from the detailed description that follows of at least a preferred embodiment of the invention, illustrated purely in the form of a non-limiting example in the accompanying figures of the drawings.

BRIEF DESCRIPTION OF THE DRAWINGS

The description of the invention will now be made with reference to the accompanying figures of the drawings, which are provided in the form of a non-limiting example, and in which.

DETAILED DESCRIPTION

Figure 1:
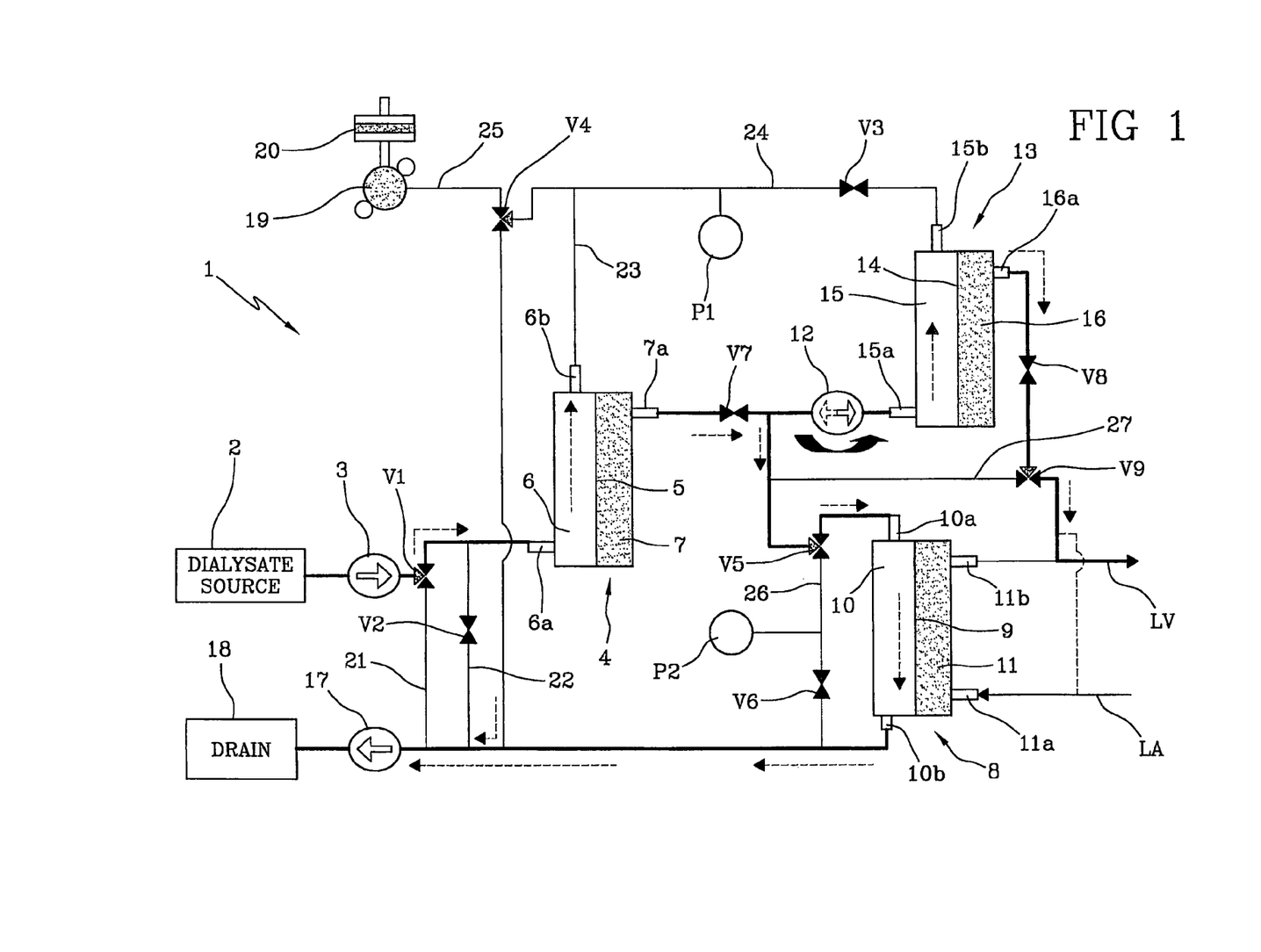
FIG. 1 is a diagram of an apparatus for hemodiafiltration to which the filter testing process of the present invention is applied.

With reference to FIG. 1, 1 denotes in its entirety an apparatus for extracorporeal blood treatment (hemodiafiltration), 2 denotes a fresh dialyser fluid, 3 a fresh dialyser fluid circulation pump, 4 a first filter having a semipermeable membrane 5 which separates a first chamber 6 from a second chamber 7, 8 a blood treatment device having a semipermeable membrane 9 which separates a dialysis chamber 10 from a blood chamber 11, 12 a replacement fluid circulation pump, 13 a second filter having a semipermeable membrane 14 which separates a first chamber 15 from a second chamber 16, 17 a used dialyser fluid drainage pump, 18 a used dialyser fluid discharge, 19 a gas pump connected to the atmosphere by a water-repelling air filter 20.

The pump 3 is arranged on a first tract of a supply line of the fresh dialysis fluid which connected the source to an inlet 6a of the first chamber 6 of the first filter 4. A second tract of the supply line connects an outlet 7a of the second chamber 7 of the first filter 4 with an inlet 10a of the device 8 dialysis chamber.

The pump 17 is arranged on a drainage line for the used dialysis fluid which connects an outlet 10b of the dialysis chamber 10 with the discharge 18.

The pump 19 is of a type which occludes the conduit it is operatively associated with when not working.

An extracorporeal blood circuit comprises an arterial line LA which takes the patient's blood to an inlet 11a of the blood chamber 11 of the device 8, and a venous line LV which returns the blood from an outlet 11b of the blood chamber 11 to the patient.

The infusion pump 12 is arranged on a first tract of an infusion line which branches from the second tract of the dialysis fluid supply line up to an inlet 15a of the first chamber 15 of the second filter 13. The pump 12 is occlusive and reversible and able to move the fluid in both circulation directions. A second tract of the infusion line connects an outlet 16a of the second chamber 16 to the extracorporeal blood circuit (for example with the venous line LV, as shown in FIG. 1, and/or the arterial line LA).

A first bypass line 21 connects the fresh dialysis fluid supply line, at a point downstream of the pump 3, to the used dialyser liquid drainage line, at a point upstream of the pump 17. A shunt valve V1 selectively directs the fluid coming from the pump 3 either towards the first filter 4 or to the first bypass line 21.

A first device, of known type and not illustrated (for example a flow meter) is predisposed on the first tract of the fresh dialyser fluid supply line, for measuring the fluid flow rate. A second device for measuring the fluid flow rate (for example, a second flow meter) is arranged on the used dialyser fluid drainage line downstream of the bypass line 21. The flow rate measuring devices enable gathering of information relating to the quantity of fluid exchanged between the extracorporeal blood and the dialysis apparatus during treatment, with the aim of controlling the patient's fluid balance, as well-known and used in dialytic treatments.

A second bypass line 22 connects the fresh dialyser fluid supply line, at a point downstream of the first bypass line 21, with the used dialyser fluid drainage line, at a point upstream of the first bypass line 21. An intercept valve V2 selectively closes or opens the second bypass line 22. The second bypass line 22 enables a rapid evacuation of liquid from the first chamber 6 of the first filter 4 in the filter checking process, as will be better explained hereinafter.

A third bypass line 23 connects an outlet 6b of the first chamber of the first filter 4 with the drainage line at a point upstream of the first bypass line 21. A fourth bypass line 24 connects an outlet 15b of the first chamber 15 of the second filter 13 with the drainage line at a point upstream of the first bypass line 21. In the preferred embodiment the third bypass line 23 and the fourth bypass line 24 have a tract in common. An intercept valve V3 selectively opens or closes the fourth bypass line 24.

A gas supply line 25 connects the gas pump 19 with the tract of bypass line in common between the bypass lines 23 and 24. A three-way valve V4 places a first way, connected to the outlets 6b and 15b of the first chambers 6 and 15 of the two filters 4 and 13, in selective communication with a second way connected to the gas pump 19, or with a third way connected to the used dialyser fluid drainage line.

A fifth bypass line 26 connects the second tract of the fresh dialyser fluid supply line, at a point downstream of the branch point of the infusion line, with the used dialyser fluid drainage line 21. A shunt valve V5 selectively directs the fluid coming from the branch point either towards the dialysis chamber 10 or to the fifth bypass line 26. An intercept valve V6 selectively closes or opens the fifth bypass line 26.

An intercept valve V7 is arranged on the second tract of the fresh dialyser fluid supply line, upstream of the branch point of the infusion line.

A connection line 27 connects the second tract of the infusion line with the second tract of the fresh dialysis fluid supply line, at a point comprised between the branching of the first tract of the infusion line and the fifth bypass line 26. An intercept valve V8 selectively opens or closes the second tract of the infusion line. A shunt valve V9 connects a first way, connected to the outlet 16a of the second chamber 16 of the second filter 13, selectively to a second way, connected to the extracorporeal circuit, or to a third way, connected to the connection line 27.

A first pressure gauge P1 measures the pressure in a tract of circuit which is connected to the outlet 6b and/or to the outlet 15b of the first chambers of the two filters 4 and 13. A second pressure gauge P2 measures the pressure in a tract of circuit connected to the outlet 7a and/or to the outlet 16a of the second chambers of the two filters 4 and 13.

FIG. 1 shows, in bold lines, the circuit lines which, during treatment, are normally crossed by the fresh or used dialysis fluid, or by the infusion liquid.

A first verification process of the integrity of the first filter 4 and the second filter 13 is now described, starting from a situation in which the apparatus is full of liquid (for example following the apparatus priming stage and before connection to the patient).

In a first filling stage of the first chambers 6 and 15 with air (see FIG. 2), the pumps 3 and 17 are active; the valve V1 directs the fluid to the first bypass line 21; the gas pump 19 operates directly, taking in air from the outside ambient; the valve V4 opens the way which is connected to the pump 19, closing the way which is connected to the drainage line; the valve V2 is opened so as to enable the air moved by the pump 19 to fill the first chamber 6 of the first filter 4, taking the place of the liquid which, driven by the pump 17, can displace, passing through the second bypass line 22; the second valve V7 is closed so that the second chamber 7 of the first filter 4 remains full of liquid; the infusion pump 12 operates inversely (with respect to the direction it takes during a treatment) while valves V3 and V6 are opened and valve V5 is opened towards the bypass line 26 and is closed towards the device 8, so that the air driven by the pump 19 can fill the first chamber 15 of the second filter 13, taking the place of the liquid removed the pump 12 and the pump 17; the valve V8 is closed and the valve V9 closes the connection line 27, so that the second chamber 16 of the second filter 13 remains full of liquid. At the end of this first stage the first chambers 6 and 15 of the two filters 4 and 13 are full of air. The arterial line LA and the venous line LV are configured so as to form a closed system which is not in communication with the external atmosphere.

Figure 2:
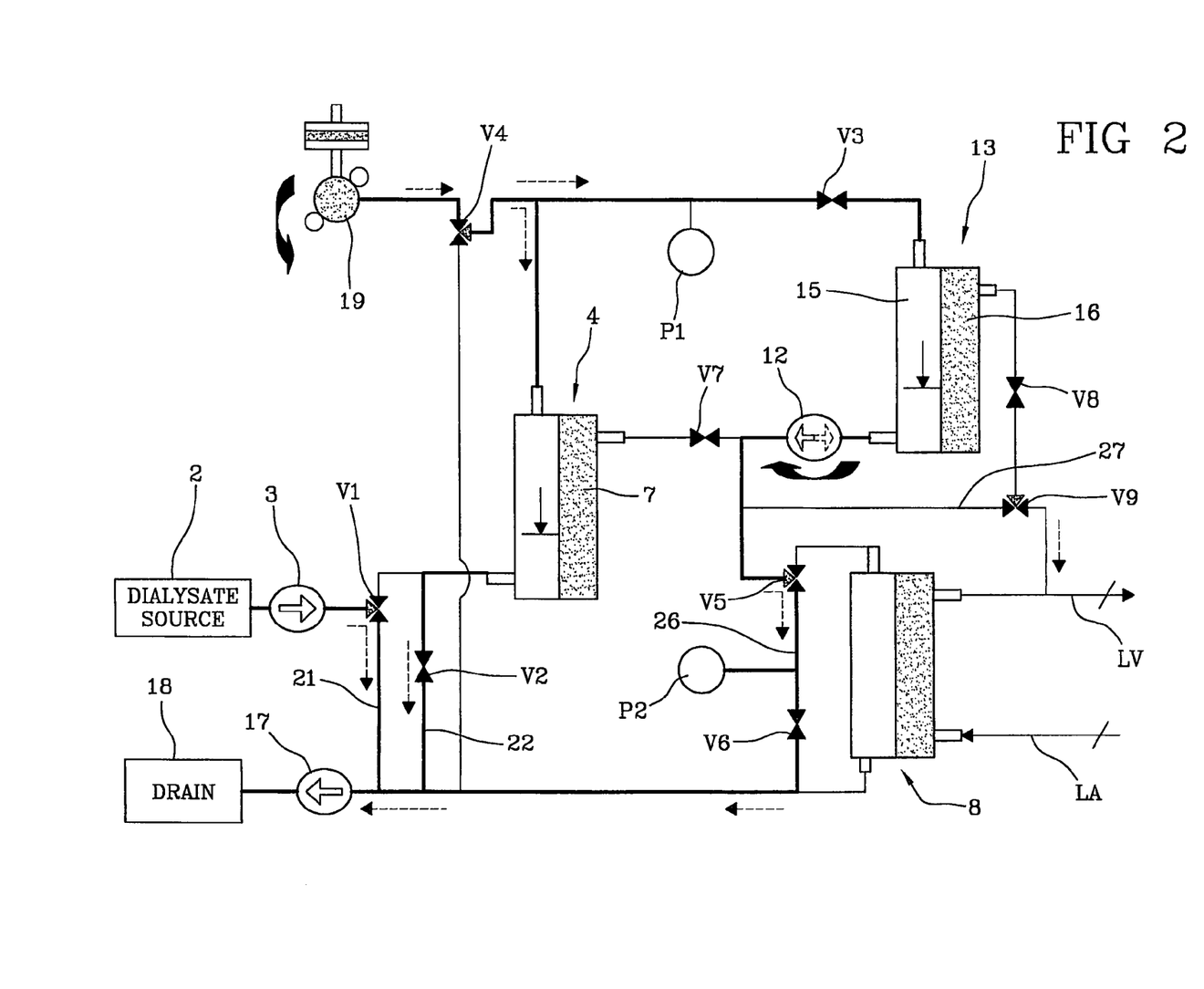
FIGS. 2, 3 and 4 show the apparatus of FIG. 1 in three different stages of the filter testing process.

FIG. 2 illustrates, in bold line, the circuit lines crossed by the fluid during the first air-filling stage.

In a second pressurising stage of the first chambers 6 and 15, (see FIG. 3), the valve V2 is closed and the infusion pump 12 (which can occlude the line) is stopped, so that the communication between the first chambers 6 and 15 and the pump 17 and the discharge 18 is closed, while the valve V3 stays open and valve V4 stays in the position which opens communication of the chambers 6 and 15 with the pump 19; the valves V7 and V8 are opened, and valve V9 opens communication with the connection line 27, in such a way that the second chambers 7 and 16 of the two filters 4 and 13 are connected to the pump 17. In this situation, in which the two membranes 5 and 14 are wet and therefore substantially impermeable to air, apart from diffusion phenomena, the gas pump 19 supplies air to the chambers 6 and 15, generating an overpressure in the chambers, while the action of the drainage pump 17 causes a depression in the chambers 7 and 16, which are full of liquid.

Figure 3:
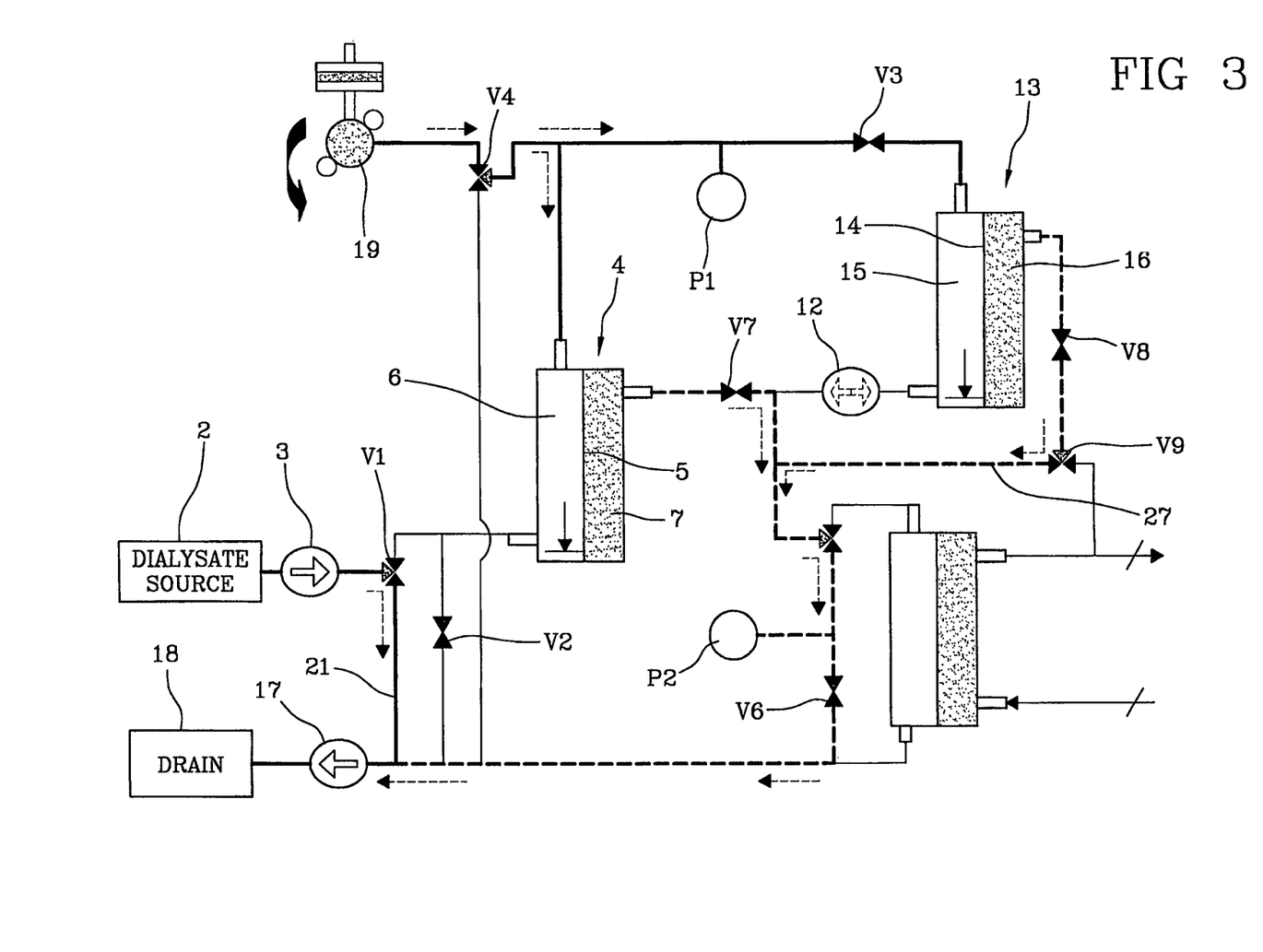

In FIG. 3 a broken line illustrates the part of the hydraulic circuit which is in depression. During this second stage, as in the first, the pump 3 continues to circulate dialyser liquid, which is deviated by the valve V1 to the bypass line 21 in order then to be sent on to the discharge 18.

The second stage terminates when the overpressure and the depression have reached a predetermined test value; basically the pump 19 stops when the pressure $P_1$ measured by the pressure gauge P1 is $P_1 > P_{max}$, where $P_{max}$ is a predetermined value; valve V6 closes, isolating chambers 7 and 16 from the pump 17, when the pressure $P_2$ measured by the pressure gauge P2 is $P_2 < P_{min}$, where $P_{min}$ is a predetermined value; in this situation (see FIG. 4) the first chambers 6 and 15 are part of a closed system in overpressure, while the second chambers 7 and 16 are part of a closed system in depression.

Figure 4:
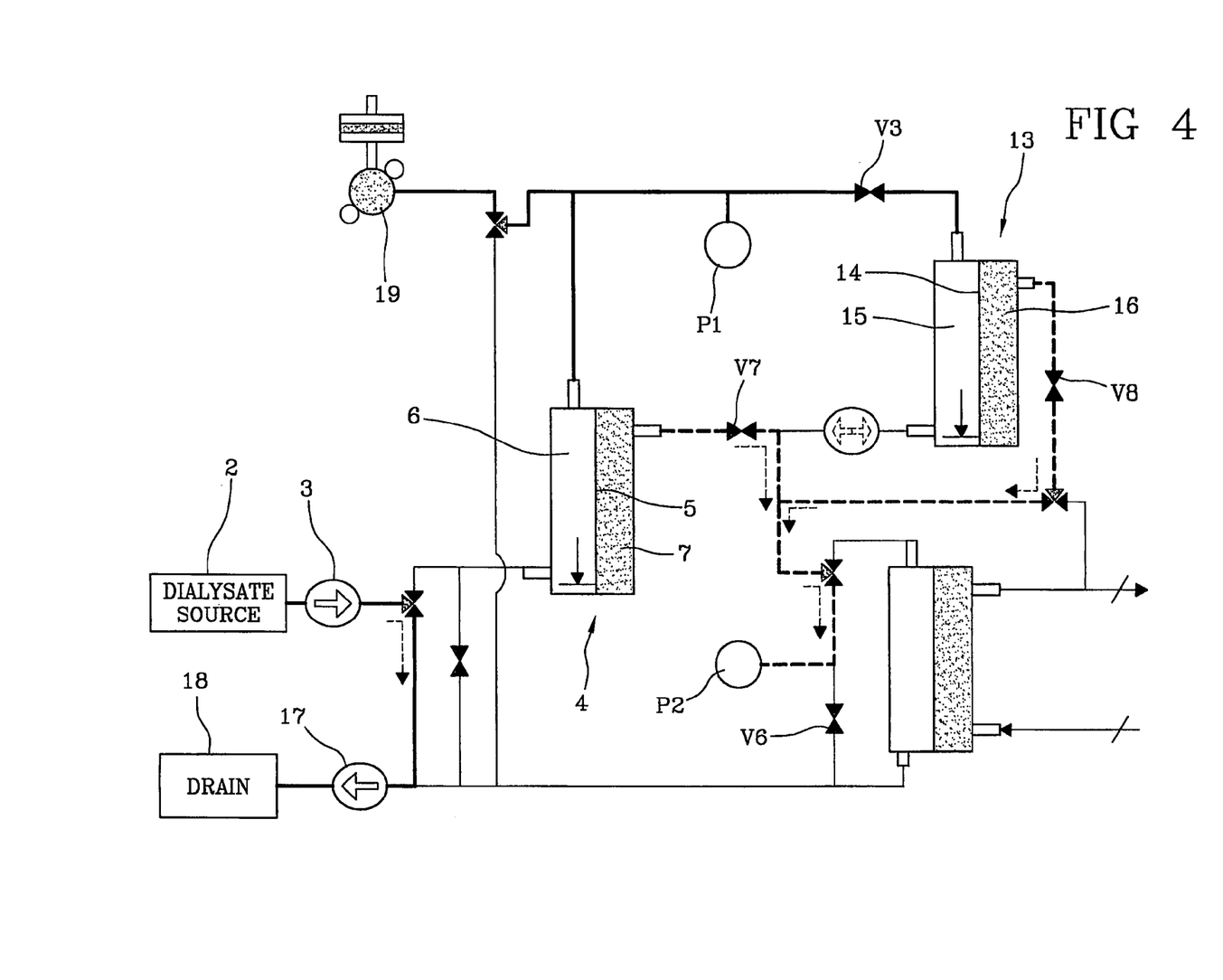

A third verification stage of the integrity of the membranes 5 and 14 includes monitoring the pressures in the pressure gauges P1 and P2, which can be performed according to various criteria, with the system in the situation illustrated in FIG. 4.

A first criterion is that after a predetermined period of time $\Delta T$, the pressure is measured by pressure gauge P1; if the pressure has dropped by a quantity $\Delta P_1 < \Delta P_{1max}$, where $\Delta P_{1max}$ is a predetermined threshold value, it is considered that the membranes 5 and 14 are intact; if, on the other hand, after time $\Delta T$, the situation is $\Delta P_1 > \Delta P_{1max}$, it is considered that at least one of the two membranes 5 and 14 is not intact, or that the closed system in overpressure which includes the chambers 6 and 15 has leaks. Alternatively it is possible to check the time the pressure P1 takes to drop beyond a predetermined limit, or to check the speed of drop of pressure P1.

With a second criterion, if, after a determined time $\Delta T$, the pressure measured at pressure gauge P2 has risen by a quantity $\Delta P_2 < \Delta P_{2max}$, where $\Delta P_{2max}$ is a predetermined threshold value, it is considered that the membranes 5 and 14 are intact; if, on the other hand after time $\Delta T$, the situation is $\Delta P_2 > \Delta P_{2max}$, it is presumed that at least one of the two membranes 5 and 14 is not intact, or that the closed system in depression which includes the chambers 7 and 16 is subject to leakage. Alternatively it is possible to verify the time required for the pressure P2 to rise beyond a predetermined limit, or to check the speed of increase of pressure P2.

With a third criterion if, after a time $\Delta T$, both $\Delta P_1 > \Delta P_{1max}$ and $\Delta P_2 > \Delta P_{2max}$ result, it is considered that one of the two membranes 5 and 14 is not intact, while if on the other hand only one of the measured pressure variations $\Delta P_1$ and $\Delta P_2$ is greater than the respective threshold value, it is considered that the membranes 5 and 14 are intact and that there is a leak in the circuit. It is possible to verify the time the pressure P1 takes to fall below a predetermined limit, and to verify the time pressure P2 takes to rise beyond a predetermined limit, and it can be decided that the membranes 5 and 14 are intact if both times exceed a predetermined minimum time. It is also possible to verify whether the speeds of change of the pressures P1 and P2 both exceed a predetermined threshold speed.

In a case, where one of the membranes 5 and 14 is not intact, a part of the air contained in the closed overpressured system which includes the chambers 6 and 15 succeeds in passing through the non-intact membrane, thanks to the compliance of the closed system in depression which includes chambers 7 and 16. This determines both a significant drop in the pressure detected by the pressure gauge P1 and a significant increase in pressure detectable by the pressure gauge P2. If a relatively large change in pressure per time unit is detected by both pressure gauge P1 and pressure gauge P2, it is concluded that one of the membranes is not intact.

The above criteria are applicable also where only one filter is verified.

In all cases, the third stage of the verification process can include a first sub-stage, in which verification is made of whether the change in pressure over the time unit exceeds a predetermined threshold, which would mean that one or the other of the membranes 5 and 14 was not intact, and a subsequent second sub-stage in which, if in the first sub-stage an excessive pressure change was detected, i.e. beyond the predetermined threshold, a valve arranged between the two chambers subjected to monitoring (for example valve V3 if the monitored chambers are chambers 6 and 15, or valve V8 if chambers 7 and 16 are monitored, or both) is closed, so that one of the two chambers is isolated from the other and the pressure gauge at work (P1 or P2 or both) is connected only to one chamber; if the excessive change in pressure continues, i.e. if the pressure gauge detects, for a second time, a pressure change which is beyond the threshold value, it is concluded that the non-intact filter is the one connected to the pressure gauge; on the other hand, if the change in pressure stops or slows down, it is concluded that the non-intact filter is the other one. If both pressure gauges P1 and P2 are used for the check, the second sub-stage is performed in such a way that each pressure gauge is connected to a different filter 4 or 13, for example by closing valves V3 and V7, so that pressure gauge P1 is connected to the first filter 4 and pressure gauge P2 is connected to the second filter 13.

In a second preferred embodiment, the verification process comprises a first stage of filling the first chambers 6 and 15 with air, as described herein before with reference to FIG. 2, and a second stage of pressurisation of the first chambers 6 and 15, at the end of which, when the overpressure and the depression have reached a respective predetermined test value, the pump 19 is stopped, as in the previous case, when the pressure $P_1$ measured by the pressure gauge P1 is $P_1 > P_{max}$, while the valves V7 and V8 stay open, keeping open the communication between the chambers 7 and 16 and the pump 17; in this situation the first chambers 6 and 15 are part of a closed system in overpressure, while the second chambers 7 and 16 are part of a non-closed system kept in depression by the pump 17 which continues to work. It is possible to use the pressure gauge P2 to control the value of the depression and keep it at a predetermined value.

There follows a third verification stage of the integrity of the membranes 5 and 14, in which, after a predetermined period of time $\Delta T$, the pressure is measured by the pressure gauge P1; if this pressure drops by an amount $\Delta P_1 < \Delta P_{1max}$, where $\Delta P_{1max}$ is a predetermined threshold value, it is concluded that membranes 5 and 14 are intact; if, on the other hand, after time $\Delta T$, the situation is $\Delta P_1 > \Delta P_{1max}$, it is concluded that at least one of the two membranes 5 and 14 is not intact, or that the closed system in overpressure which includes chambers 6 and 15 is leaking.

During the above-described third stage, the pump 17 is controlled in order to maintain the predetermined depression value inside the chambers 7 and 16. The depression maintained in the chambers 7 and 16 enables an increase to be made in the transmembrane pressure gradient, without increasing the gas overpressure in the chambers 6 and 15, thus without any further strain on the hydraulic circuit.

The verification process of the second preferred embodiment is also applicable to a single filter.

In the process of the second preferred embodiment a first variant can be included, in which during the third monitoring stage the liquid flow is measured as it exits the chambers 7 and 16 of the filters, for example using the difference of the flow rate values measured by the flow meters that the HDF apparatus uses during the treatment for the patient's fluid balance. The liquid flow rate corresponds to the air flow rate passing through the membrane, entering the chambers 7 and 16, which is indicative of the state of the membranes 5 and 14. While the liquid flow rate is measured, the depression $P_2$ in the chambers 7 and 16 is maintained constant at a predetermined value, for example comprised between 0.2 and 0.9 bar (absolute pressure). If the liquid flow rate measured exceeds a predetermined threshold value, it is considered that at least one of the two membranes 5 and 14 is not intact, and exhibits breakage, leakage, or has too-large pores or excessive permeability.

In the process of the second preferred embodiment, a second variant can be included in which, in addition to the first variant, not only the depression $P_2$ but also the overpressure $P_1$ in the first chambers 6 and 15 is kept at a constant predetermined value, for example comprised between 1.2 and 3.0 bar (absolute pressure), by activating the pump 19 which supplies the air that passes through the membranes 5 and 14. The air flow supplied by the pump 19 (which can be calculated for example from the pump speed, being a positive displacement pump) corresponds to the flow rate measured for the liquid exiting from the chambers 7 and 16. Thus, the air flow rate is also indicative of the state of the membrane. In this second variant of the second preferred embodiment of the process, the first chambers 6 and 15 are maintained at a constant overpressure by the pump 19, while the second chambers 7 and 16 are kept at a constant depression by the pump 17; the state of the membrane is evaluated by the air flow rate passing through the membranes 5 and 14 from the first chambers to the second chambers, the flow rate being calculable either by measuring the liquid flow rate exiting the second chambers 7 and 16, or by measuring the air flow rate supplied to the first chambers 6 and 15, or by both of the above-mentioned measurements.

The two above-described variants of the second embodiment of the testing process are applicable to a single filter.

In a third embodiment, the process for verifying the filters 4 and 13 includes filling the chambers 6 and 15 with air, generating a depression in the liquid-filled chambers 7 and 16, forming a closed system which includes the chambers 7 and 16, and monitoring the depression in the chambers 7 and 16. The filters are considered to be intact for example if, after a predetermined time $\Delta T$, the pressure measured by the pressure gauge P2 has risen by an amount $\Delta P_2 < \Delta P_{2max}$, where $\Delta P_{2max}$ is a predetermined threshold value.

The testing processes described above can also be applied to a dialysis filter.

Figures from 5 to 8 relate to testing processes applied to a single filter of an apparatus for extracorporeal blood treatment.

Figure 5:
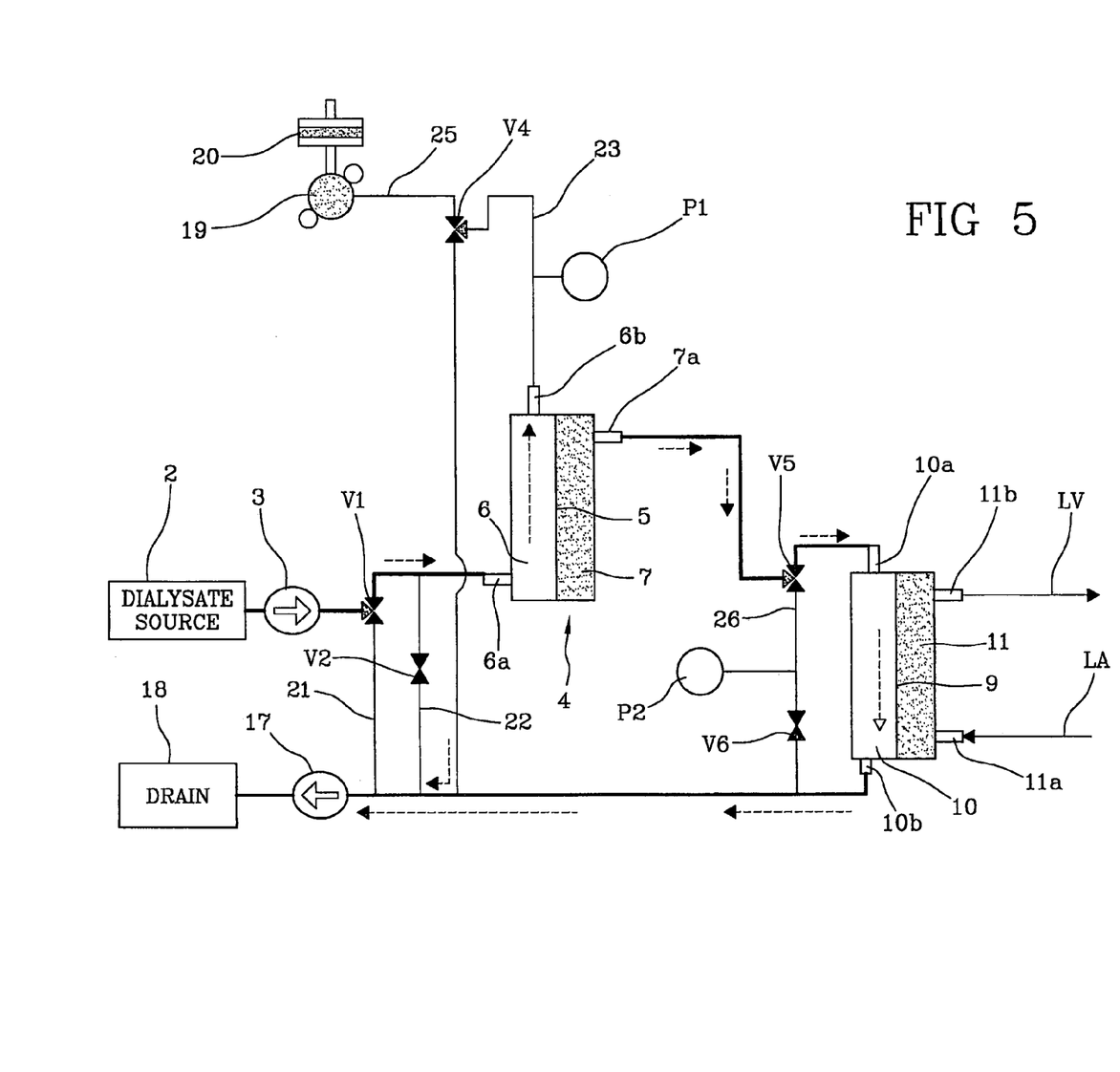
FIG. 5 is a diagram of a hemodialysis apparatus to which the process for testing filters of the present invention is applied.
Figure 6:
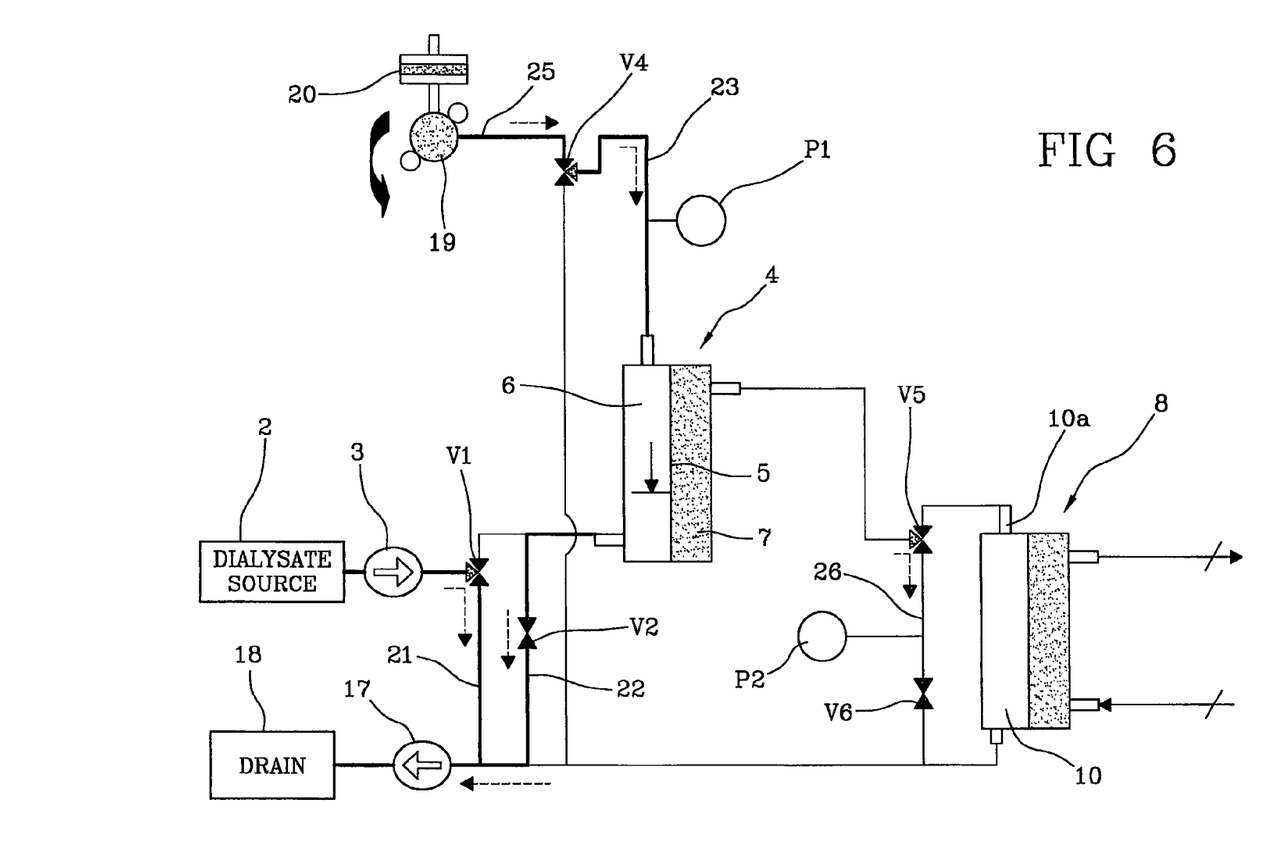
FIGS. 6, 7 and 8 show the apparatus of FIG. 5 in three different stages of the filter testing process of the invention.

FIG. 5 shows an apparatus for dialysis in which the elements that are similar to the apparatus of FIG. 1 have been indicated for reasons of simplicity using the same enumeration.

A first testing process of the filter 4, starting from a situation in which the membrane 5 is wet and the chambers 6 and 7 are both full of liquid, comprises a first emptying stage of liquid from the first chamber 6 and a filling thereof with air coming from the pump 19. In this first stage (see FIG. 6), the situation is as follows: the pump 17 removes the liquid from the first chamber 6 and sends it towards the discharge 18 with the valve V2 open. The air coming from the outside environment through the hydrophobic filter 20 is supplied by the pump 19 to the first chamber 6 with the valve V4 open towards the pump 19 and closed towards the drainage line, the valve V5 opens toward the bypass 26 and closes towards the port 10a of the dialyser; the valve V6 closes the bypass 26 so that the second chamber 7 does not communicate with the operating pump 17 and remains full of liquid. At the end of this first stage the first chamber 6 is full of air and the second chamber 7 is still full of liquid.

In a second stage (FIG. 7) the first chamber 6 is placed in overpressure and the second chamber 7 in depression: the valve V2 is closed and the pump 19 continues to supply air to the first chamber 6; the valve V6 is open so that the pump 17 communicates with the second chamber 7; the pressure gauges P1 and P2 send the relative pressure signals to a control unit of the apparatus which, as in an example already described herein before, controls the pump 19 so as to maintain a constant overpressure in the first chamber 6 (for example at a value comprised between 1.2 and 3.0 bar in absolute pressure), and the pump 17 so as to maintain a constant depression in the second chamber 7 (for example at a value comprised between 0.2 and 0.9 bar of absolute pressure); the state of the membrane 5 is calculated on the basis of the air flow rate which, in this situation of constant pressures, enters the first chamber 6 and/or the liquid flow rate exiting the second chamber 7. As previously mentioned, these flow rates can be calculated from the speed of the positive displacement pump 19 and the flow rate data provided by the device the apparatus is provided with for maintaining the fluid balance of the patient during the dialysis treatment. For example, the fluid balancing device can comprise two flow meters (not illustrated) arranged with one on the fresh dialysis fluid supply line and the other on the used fluid drainage line, so that the liquid flow rate exiting the second chamber 7 can be determined by the difference of the flow rates measured by the two flow meters. Obviously other fluid balance devices, of known type for a dialysis apparatus, can be used in order to calculate the liquid flow rate exiting from the chamber 7.

Figure 7:
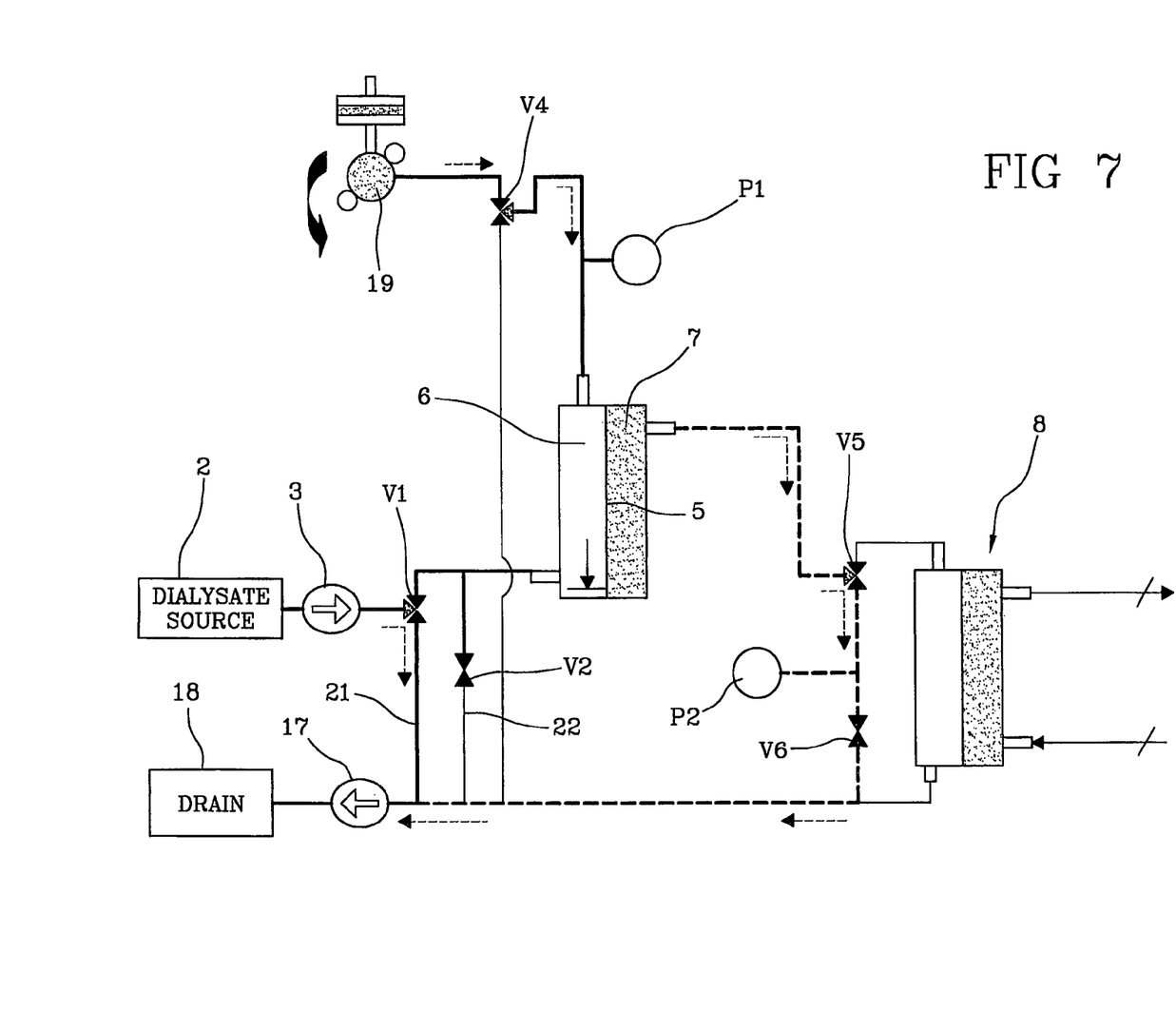

If both flow rates exceed a threshold value, it is considered that the membrane 5 is not suitable (for example because it exhibits breakages, leaks, too-large pores and so on). If the two flow rates differ from each other by a predetermined threshold value, it is considered that the membrane is suitable and that there is a leak in the part of the hydraulic circuit on the side where the greater flow rate is measured.

Alternatively to the above process, it is possible to form two closed circuits, each of which includes one of the two chambers 6 and 7, one in overpressure and the other in depression, and to monitor over time the changes in pressure in one or both of the closed systems; a first system (indicated by a long broken lines in FIG. 8) which includes the first chamber 6 and the first pressure gauge P1, is defined between the closed valve V2 and the pump 19 when the latter is still; a second system (indicated with short broken lines in FIG. 8), which includes the second chamber 7 and the second pressure gauge P2, is defined by the closure of the valve V6. In the case of a non-intact or unsuitable membrane (because it exhibits breakages, leakage, too-large pores etc.) a drop in pressure obtains in the first system connected to the pressure gauge P1 and an increase in pressure obtains in the second system connected to the pressure gauge P2, due to a passage of air from the first to the second chamber through the membrane 5, which passage is allowed, as has previously been described, thanks to the compliance of the liquid-filled second system.

Figure 8:
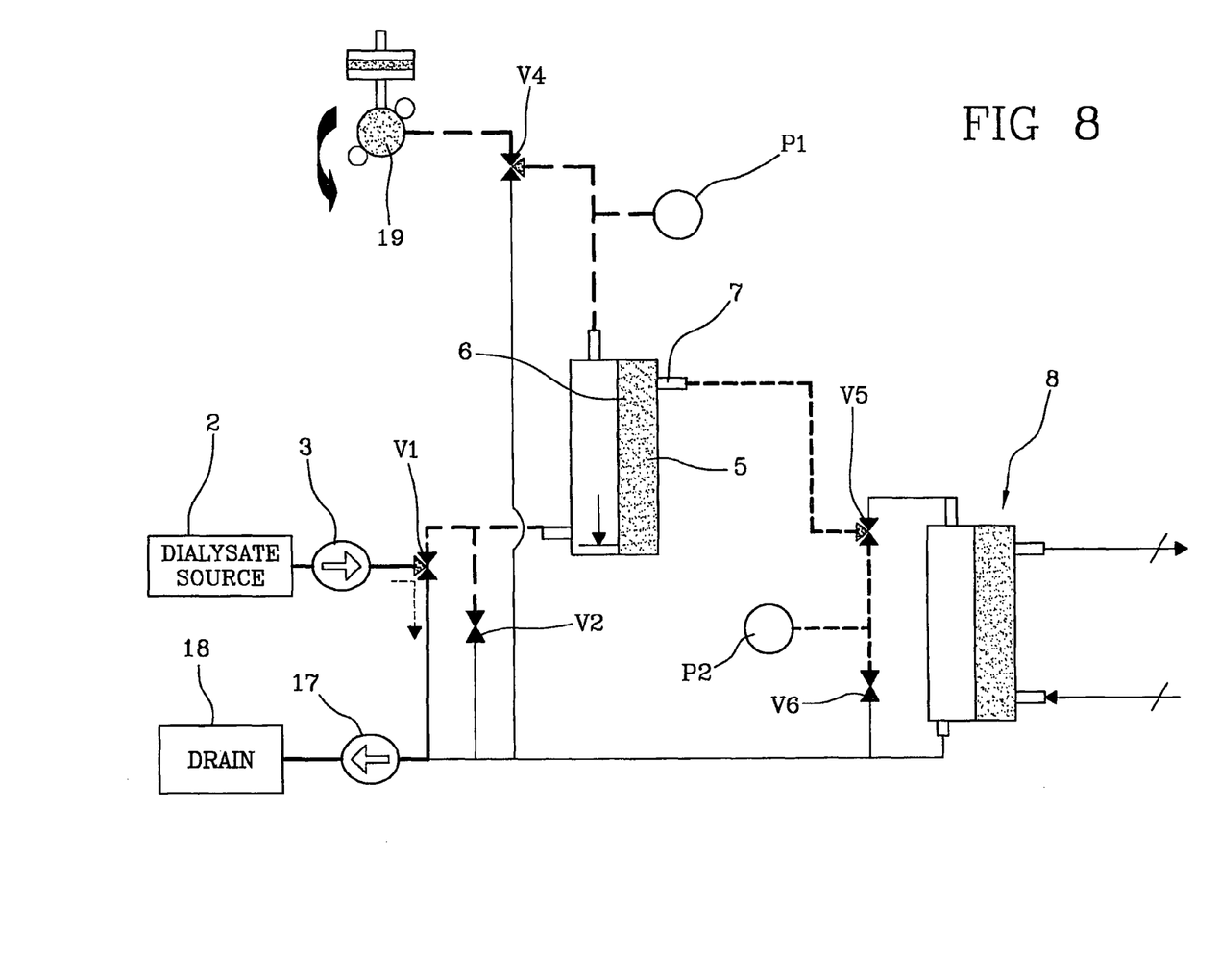

A further testing process is also possible, in which a first closed system is formed in air overpressure which includes the first chamber 6, while the second chamber 7 is maintained at a constant depression by the pump 17, keeping the valve V6 open. In this case the monitoring stage includes reading the liquid flow exiting the second chamber 7 (as already described herein-above), as well as the drop in pressure at the pressure gauge P1. In the case that both the liquid flow rate and the pressure drop exceed respective threshold values, the membrane is considered to be unsuitable.

A further process consists in maintaining a constant air overpressure in the first chamber 6 by means of the pump 19, while the second chamber 7 is part of a closed system in depression with the valve V6 closed. In this case the monitoring stage includes a monitoring of the increase in pressure at the pressure gauge P2 and reading the air flow entering the first chamber 6 and thus the second chamber 7 due to the compliance of the closed system the chamber 7 is part of. If both the air flow and the pressure increase exceed respective threshold values, the membrane is considered to be unsuitable.

The verification processes described above in relation to the dialysis apparatus of FIG. 5 are also applicable to a hemodiafiltration apparatus comprising, for example, an infusion pump arranged on an infusion line which branches from the dialysis fluid supply line and which incorporates a filter for the infusion fluid, similarly to the apparatus of FIG. 1.

The invention claimed is:

1. An apparatus for testing a filter, comprising:
   a source of a fluid for an extracorporeal blood treatment;
   a supply line connected to the source;
   a blood treatment device having a semipermeable membrane which separates a fluid chamber connected to the supply line from a blood chamber connected to an extracorporeal blood circuit;
   a drainage line which connects the fluid chamber with a discharge of a used treatment fluid;
   at least a bypass line arranged between the supply line and the drainage line;
   a filter having a semipermeable membrane which separates a first chamber from a second chamber, the first chamber having at least a first fluid port connected to the supply line, the second chamber having at least a second fluid port directly connected to the supply line, the first chamber having at least a third fluid port directly connected to the bypass line;
   means for generating a pressure gradient between the first chamber and the second chamber, the means for generating a pressure gradient comprising means for generating, in the first chamber, a pressure above atmospheric pressure, and means for generating, in the second chamber, a pressure below atmospheric pressure, the means for generating a pressure above atmospheric pressure comprising means for supplying a gas to the first chamber through the third fluid port, the means for supplying a gas comprising a gas pump connected at a side thereof with an outside ambient and at an opposite side thereof with the bypass line, the means for generating a pressure below atmospheric pressure comprising a drainage pump arranged on the drainage line;
   a gas supply line directly connecting the gas pump to the bypass line;
   a valve arrangement which places the third fluid port in selective communication with the gas pump or with the drainage line;
   means for monitoring a pressure in the first chamber and/or in the second chamber;
   a controller connected to the means for generating a pressure gradient and to the means for monitoring the pressure, and being configured to carry out the steps of:
   generating a pressure gradient between the first chamber and the second chamber, by driving the gas pump to create in the first chamber a first pressure which is above atmospheric pressure and by driving the drainage pump to create in the second chamber a second pressure which is below atmospheric pressure;

monitoring a pressure in the first chamber and/or in the second chamber.

2. The apparatus of claim 1, wherein the gas pump is connected with the outside ambient through a hydrophobic filter, and with the bypass line through a valve.

3. The apparatus of claim 1, comprising:
at least a first further bypass line which connects a second tract of the supply line with a second tract of the drainage line, the second tract of the supply line being arranged between the second chamber of the filter and the fluid chamber of the blood treatment device and the second tract of the drainage line being arranged upstream of the drainage pump.

4. The apparatus of claim 1, wherein the valve arrangement comprises a three-way valve selectively directing the gas coming from the gas supply line towards the first chamber of the filter or directing the fluid from the second fluid port towards the drainage line.

5. The apparatus of claim 3, comprising a first and a second bypass valve arranged on the first further bypass line, wherein the first bypass valve selectively directs a fluid coming from the supply line either towards the second chamber of the blood treatment device or towards the second bypass valve, the second bypass valve selectively closing or opening the first further bypass line.

6. The apparatus of claim 3, comprising:
a supply pump arranged on the supply line upstream of the first chamber;
at least a second further bypass line which connects a first tract of the supply line with the second tract of the drainage line, the first tract of the supply line being arranged between the supply pump and the first chamber; and
a bypass valve arranged on the second further bypass line, the controller being configured to carry out the step of directing the fluid form the source of a fluid towards the discharge through said second further bypass line.

7. The apparatus of claim 3, comprising:
a supply pump arranged on the supply line upstream of the first chamber;
at least a third further bypass line which connects a first tract of the supply line with the second tract of the drainage line, the first tract of the supply line being arranged between the supply pump and the first chamber; and
a bypass valve arranged on the third further bypass line, the controller being configured to carry out the step of directing the fluid form the first fluid port of the first chamber of the filter towards the drainage line through said third further bypass line.

8. An apparatus for testing a filter, comprising:
a source of a fluid for an extracorporeal blood treatment;
a supply line connected to the source;
a blood treatment device having a semipermeable membrane which separates a fluid chamber connected to the supply line from a blood chamber connected to an extracorporeal blood circuit;
a drainage line which connects the fluid chamber with a discharge of a used treatment fluid;
at least a bypass line arranged between the supply line and the drainage line;
a filter having a semipermeable membrane which separates a first chamber from a second chamber, the first chamber having at least a first fluid port connected to the supply line, the second chamber having at least a second fluid port directly connected to the supply line, the first chamber having at least a third fluid port directly connected to the bypass line;

means for generating a pressure gradient between the first chamber and the second chamber, the means for generating a pressure gradient comprising means for generating, in the first chamber, a pressure above atmospheric pressure, and means for generating, in the second chamber, a pressure below atmospheric pressure, the means for generating a pressure above atmospheric pressure comprising means for supplying a gas to the first chamber through the third fluid port, the means for supplying a gas comprising a gas pump connected at a side thereof with an outside ambient, the means for generating a pressure below atmospheric pressure comprising a drainage pump arranged on the drainage line;

a gas supply line which leads from the gas pump to the bypass line;

means for monitoring a pressure in the first chamber and/or in the second chamber;

at least a first further bypass line which connects a second tract of the supply line with a second tract of the drainage line, the second tract of the supply line being arranged between the second chamber of the filter and the fluid chamber of the blood treatment device and the second tract of the drainage line being arranged upstream of the drainage pump, a controller connected to the means for generating a pressure gradient and to the means for monitoring the pressure and being configured to carry out the steps of:

generating a pressure gradient between the first chamber and the second chamber, the first chamber having a first pressure which is above atmospheric pressure and the second chamber having a second pressure which is below atmospheric pressure; the step of generating a pressure gradient comprises supplying a gas to the first chamber through the third fluid port;

monitoring a pressure in the first chamber and/or in the second chamber.

9. The apparatus of claim 8, wherein the controller is configured carry out the further step of filling the first chamber with gas through the third fluid port and by evacuating a liquid from the first chamber through the first fluid port.

10. An apparatus for testing a filter, comprising:
a source of a fluid for an extracorporeal blood treatment;
a supply line connected to the source;
a blood treatment device having a semipermeable membrane which separates a fluid chamber connected to the supply line from a blood chamber connected to an extracorporeal blood circuit;
a drainage line which connects the fluid chamber with a discharge of a used treatment fluid;
at least a bypass line arranged between the supply line and the drainage line;
a first filter having a semipermeable membrane which separates a first chamber of the first filter from a second chamber of the first filter, the first chamber of the first filter having at least a first fluid port connected to the supply line, the second chamber of the first filter having at least a second fluid port directly connected to the supply line, the first chamber of the first filter having at least a third fluid port directly connected to the bypass line;
at least a first further bypass line which connects a second tract of the supply line with a second tract of the drainage line, the second tract of the supply line being arranged between the second chamber of the first filter and the fluid chamber of the blood treatment device and the second tract of the drainage being arranged upstream of the drainage pump;

a second filter having a semipermeable membrane which separates a first chamber of the second filter from a second chamber of the second filter, the first chamber of the second filter having at least a first fluid port connected to the second tract of the supply line, the second chamber of the second filter having a second port, and the first chamber of the second filter having a third port connected to the third port of the first filter, an infusion line having a first tract, which branches from the second tract of the supply line and which connects to the first port of the second filter, and a second tract, which connects the second port of the second filter to the extracorporeal blood circuit, means for generating a pressure gradient between the first chamber and the second chamber of the first filter and between the first chamber and the second chamber of the second filter, the means for generating a pressure gradient comprising means for generating, in the first chambers, a pressure above atmospheric pressure, and means for generating, in the second chambers, a pressure below atmospheric pressure, the means for generating a pressure above atmospheric pressure comprising means for supplying a gas to the first chambers through the third fluid ports, the means for supplying a gas comprising a gas pump connected at a side thereof with an outside ambient, the means for generating a pressure below atmospheric pressure comprising a drainage pump arranged on the drainage line;

a gas supply line which leads from the gas pump to the bypass line;

means for monitoring a pressure in the first chamber and/or in the second chamber;

a controller connected to the means for generating a pressure gradient and to the means for monitoring the pressure, and being configured to carry out the steps of:

generating a pressure gradient between the first chambers and the second chambers by supplying gas to the first chambers and generating a first pressure which is above atmospheric pressure and by generating a second pressure which is below atmospheric pressure in the second chambers;

monitoring a pressure in the first chamber and/or in the second chamber.

11. The apparatus of claim 8, comprising a first and a second bypass valves arranged on the first further bypass line, wherein the first bypass valve selectively directs a fluid coming from the supply line either towards the fluid chamber of the blood treatment device or towards the second bypass valve, the second bypass valve selectively closing or opening the first further bypass line.

12. The apparatus of claim 8, comprising:
a supply pump arranged on the supply line upstream of the first chamber;
at least a second further bypass line which connects a first tract of the supply line with the second tract of the drainage line, the first tract of the supply line being arranged between the supply pump and the first chamber; and
a bypass valve arranged on the second further bypass line, the controller being configured to carry out the step of directing the fluid form the source of a fluid towards the discharge through said second further bypass line.

13. The apparatus of claim 8, comprising:
a supply pump arranged on the supply line upstream of the first chamber;
at least a third further bypass line which connects a first tract of the supply line with the second tract of the drainage line, the first tract of the supply line being arranged between the supply pump and the first chamber; and
a bypass valve arranged on the third further bypass line, the controller being configured to carry out the step of directing the fluid form the first fluid port of the first chamber of the filter towards the drainage line through said third further bypass line.

14. The apparatus of claim 10, comprising a first and a second bypass valves arranged on the first further bypass line, wherein the first bypass valve selectively directs a fluid coming from the supply line either towards the fluid chamber of the blood treatment device or towards the second bypass valve, the second bypass valve selectively closing or opening the first further bypass line.

15. The apparatus of claim 10, comprising:
a supply pump arranged on the supply line upstream of the first chamber;
at least a second further bypass line which connects a first tract of the supply line with the second tract of the drainage line, the first tract of the supply line being arranged between the supply pump and the first chamber; and
a bypass valve arranged on the second further bypass line, the controller being configured to carry out the step of directing the fluid form the source of a fluid towards the discharge through said second further bypass line.

16. The apparatus of claim 10, comprising:
a supply pump arranged on the supply line upstream of the first chamber;
at least a third further bypass line which connects a first tract of the supply line with the second tract of the drainage line, the first tract of the supply line being arranged between the supply pump and the first chamber; and
a bypass valve arranged on the third further bypass line, the controller being configured to carry out the step of directing the fluid form the first fluid port of the first chamber of the filter towards the drainage line through said third further bypass line.

* * * * *